(12) United States Patent
Wilkes

(10) Patent No.: US 8,632,596 B2
(45) Date of Patent: Jan. 21, 2014

(54) TEMPOROMANDIBULAR JOINT REPLACEMENT APPARATUS AND METHODS

(75) Inventor: Clyde Hawthorne Wilkes, Fernandina Beach, FL (US)

(73) Assignee: Brad Kieley, Maple Plain, MN (US)

( * ) Notice: Subject to any disclaimer, the term of this patent is extended or adjusted under 35 U.S.C. 154(b) by 61 days.

(21) Appl. No.: 12/957,677

(22) Filed: Dec. 1, 2010

(65) Prior Publication Data

US 2011/0137422 A1 Jun. 9, 2011

Related U.S. Application Data

(60) Provisional application No. 61/266,655, filed on Dec. 4, 2009.

(51) Int. Cl.
*A61F 2/30* (2006.01)
(52) U.S. Cl.
USPC ........................................................ 623/17.17
(58) Field of Classification Search
USPC .......................................... 623/17.17–17.19
See application file for complete search history.

(56) References Cited

U.S. PATENT DOCUMENTS

| 4,936,852 A * | 6/1990 | Kent et al. ................... 623/17.17 |
| 5,593,445 A | 1/1997 | Waits |
| 2008/0208346 A1 | 8/2008 | Schwartz |
| 2009/0222102 A1 | 9/2009 | Deffrennes |

OTHER PUBLICATIONS

Wright Medical Technology, "Profemur Z: Total Hip System", Wright Medical Technology, Inc., MH 183-703 2003.

* cited by examiner

*Primary Examiner* — David Isabella
*Assistant Examiner* — Ann Schillinger
(74) *Attorney, Agent, or Firm* — Pauly, DeVries Smith & Deffner, L.L.C.

(57) ABSTRACT

Embodiments of the invention are related to temporomandibular joint replacement apparatus and methods, amongst other things. In an embodiment, the invention includes an apparatus for treating dysfunction of the temporomandibular joint including a base plate comprising a bottom surface defining a tongue, and a surface plate comprising a substantially convex surface. The surface plate can be configured to be fastened to the base plate. Other embodiments are also included herein.

6 Claims, 9 Drawing Sheets

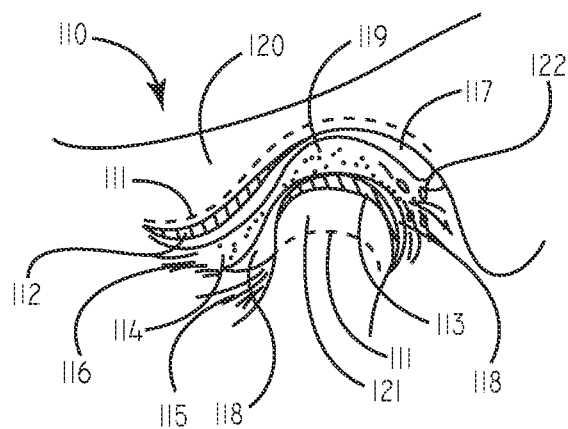

US 8,632,596 B2

TEMPOROMANDIBULAR JOINT REPLACEMENT APPARATUS AND METHODS

This application claims the benefit of U.S. Provisional Application No. 61/266,655, filed Dec. 4, 2009, the content of which is herein incorporated by reference in its entirety.

TECHNICAL FIELD

This disclosure relates generally to medical devices and, more particularly, to apparatus and methods for replacing the temporomandibular joint, amongst other things.

BACKGROUND OF THE INVENTION

Although there are many possible causes of detrimental and pathological changes in the integrity and function of the temporomandibular joint (TMJ), one of the most common is the long term sequelae of internal derangements.

A late stage internal derangement of the TMJ constitutes complete anterior dislocation of the disk, usually of many years duration, along with progressive degenerative changes of the joint, both hard and soft tissues, and even possible collapse of posterior facial height with subsequent facial deformity and major occlusal changes. The principle pathologic finding in such cases is irreversible damage to articular bearing surfaces of the articular eminence and condyle head. The surfaces are usually found to be degenerated, remodeled and with roughened, fibrillated fibrocartilage, and direct bone on bone articular contact. Only remnants of the anteriorly dislocated degenerated articular disk remain. Usually a perforation is present in the disk posterior attachment region, through which the damaged articulating surfaces are in contact. Patients complain of a grating sound symptom in this condition and the corresponding medical physical sign on direct palpation is "crepitus", which is nearly always present. Joint pain and dysfunction can become unremitting and significant quality of life issues become evident.

Numerous conservative and operative procedures have been used over the years to ameliorate symptoms of TMJ pain and dysfunction. In particular, for advanced conditions as described above there have been attempts to surgically replace damaged bearing surfaces in the TMJ. Nearly all such procedures have necessitated major resection of boney parts of the TMJ with complete or partial removal of the condyle as well as marked resection or removal of the articular eminence.

Such procedures are characterized by the use extra-articular fixation methods (outside of the joint capsule) with multiple screws and bone cement. Most procedures involve long metal shanks covering a good portion of the mandibular ramus with multiple bone screws to fixate the condyle portion of the joint and similar methods with screws and bone cement to fixate the articular eminence and/or upper bearing surface replacement.

It is noteworthy also in such procedures that various masticatory muscles are elevated from their boney surface attachments and specifically the attachment of the lower head of the lateral pterygoid muscle to the mandibular condyle is removed. This is likely to result in near complete loss of translatory and lateral movement of the condyle and mandible on the affected side and thus significant impairment in normal masticatory function. Elevation of both superficial and deep heads of the masseter muscle is required as well as an additional incision in the neck area in order provide access for mandibular/condyle fixation.

The overall result of current day total joint TMJ implant device procedures is a complex mechanical affair heavy in volume and weight of implant materials. Such procedures necessitate highly invasive surgical procedures with extensive resection of joint structures and multiple extensive incisions in the facial and neck region for access purposes and subsequent prolonged hospitalizations. Such procedures also carry a significant risk of infection because of the mass of implant material involved. In some case, there may also be other undesirable developments such as the formation of fibrous adhesions in and around joint structures with accompanying restriction of motion as well as excessive reactive boney exostosis.

SUMMARY OF THE INVENTION

Embodiments of the invention are related to temporomandibular joint replacement apparatus and methods, amongst other things. In an embodiment, the invention includes an apparatus for treating dysfunction of the temporomandibular joint including a base plate comprising a bottom surface defining a tongue, and a surface plate comprising a substantially convex surface. The surface plate can be configured to be fastened to the base plate.

In an embodiment, the invention includes an apparatus for treating dysfunction of the temporomandibular joint including a base plate, a surface plate comprising a substantially convex surface, and an insert configured to fit between the base plate and the surface plate. The insert can be configured to facilitate locking of the surface plate to the base plate.

In an embodiment, the invention includes a method of treating dysfunction of the temporomandibular joint including removing bone from the condyle head to form a surface defining a groove, inserting a base plate comprising a tongue into the condyle head with the tongue fitting into the groove, and attaching a surface plate over the base plate.

In an embodiment, the invention includes an apparatus for treating dysfunction of the temporomandibular joint including a condyle assembly comprising a bottom surface defining a tongue and a top surface comprising a substantially convex surface.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

BRIEF DESCRIPTION OF THE DRAWINGS

The invention may be more completely understood in connection with the following drawings, in which:

FIG. 1 is a schematic side view of the TMJ in a closed mouth position (teeth in centric occlusion) showing normal joint structures including joint spaces, articular disk and disk attachments.

FIG. 2 is a schematic side view of the TMJ in an open mouth position demonstrating rotation and translation of mandibular condyle and normal movement of articular disk and attachments.

Figure 3:
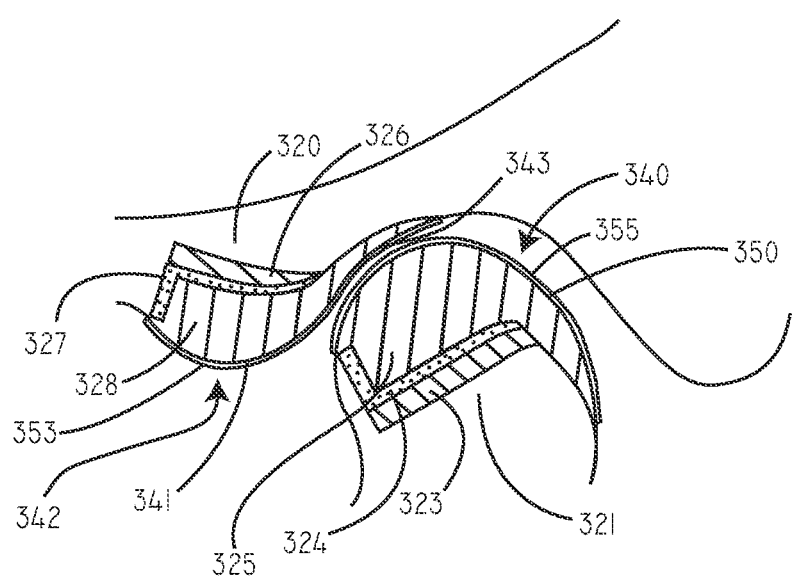
FIG. 3 is a schematic side view of a condyle assembly and articular eminence assembly implanted within the TMJ in accordance with various embodiments herein.

While the invention is susceptible to various modifications and alternative forms, specifics thereof have been shown by way of example and drawings, and will be described in detail. It should be understood, however, that the invention is not limited to the particular embodiments described, which are provide as examples. On the contrary, the intention is to cover modifications, equivalents, and alternatives falling within the spirit and scope of the invention.

DETAILED DESCRIPTION

Embodiments herein can include an apparatus for treating dysfunction of the temporomandibular joint. In an embodiment, the apparatus can include a condyle assembly including a base plate having a bottom surface defining a tongue and a surface plate with a substantially convex surface, the surface plate configured to be fastened to the base plate. The apparatus can further include an articular eminence assembly including a base plate having a bottom surface defining a tongue and a surface plate with a substantially convex surface, the surface plate configured to be fastened to the base plate. In various embodiments, both the condyle assembly and the articular eminence assembly can fit completely within the capsular space of the TMJ joint.

Various embodiments included herein can be implanted using a minimally invasive procedure. In some embodiments, a method of treating dysfunction of the temporomandibular joint can include removing bone from the condyle head to form a surface defining a groove, inserting a base plate comprising a tongue into the condyle head with the tongue fitting into the groove, and attaching a surface plate over the base plate. Similarly, a method of treating dysfunction of the temporomandibular joint can include removing bone from the articular eminence to form a surface defining a groove, inserting a base plate comprising a tongue into the articular eminence with the tongue fitting into the groove, and attaching a surface plate over the base plate.

It will be appreciated that embodiments described herein can achieve various advantages. In addition to minimally invasive implantation, some embodiments herein can be implanted relatively quickly leading to a procedure more conducive to out-patient surgery. In addition, in some embodiments, the need to cut tissues (such as removal of the attachment of the lower head of the lateral pterygoid muscle to the mandibular condyle) is substantially reduced or eliminated leading to quicker recovery times and better long-term use of the joint. In various embodiments herein, the sheer amount of material implanted is significantly less than with various known techniques which is believed to lead to a substantially lower risk of infection. Embodiments herein can also facilitate use of the TMJ joint in a more natural manner wherein the jaw is free to move as a normal jaw would (including forward and lateral translation) leading to enhanced post-surgical use of the joint. In some embodiments herein, the surface of the implant that is subject to wear can be replaced if needed without revising the entire implant. By way of example, in some embodiments, the surface plate can be removed without disturbing the attachment of the base plate to the bone and a new surface plate can be fitted. While these are some of the advantages associated with certain of the embodiments herein, it will be appreciated that not every embodiment falling within the scope of the claims herein will necessarily achieve all of these possible advantages.

FIG. 1 shows a normal TMJ 110 in closed mouth view with the teeth in centric occlusion and the condyle 121 seated in its most posterior and superior position. The view as shown is slightly distracted to show detail of the associated upper bearing surface 112 of the articular eminence 120, the articular disk (posterior band 119 and anterior band 114) and the lower bearing surface 113 of the condyle 121. The capsule attachment 111 (shown as a dashed line) is shown for the upper and lower joint. The inner surface of the capsule along with upper joint space 117 and lower joint space 118 forms a lateral recess space. The anterior and posterior recesses of the upper, lower and lateral joint spaces are lined with synovial tissue. The upper head of the lateral pterygoid muscle is inserted into the anterior medial aspect of the disk 116 and the lower head of the lateral pterygoid muscle is inserted into the neck of the condyle at its anterior margin 115.

FIG. 2 shows the normal TMJ 110 in open mouth view, slightly distracted in order to demonstrate detail. As can be seen, the condyle 121 has undergone translation and rotation. The central articulating area of the disk is now between the upper bearing surface 112 and the lower bearing surface 113. The elastic posterior attachment 122 has stretched as the disk is pulled forward by the upper head of the lateral pterygoid muscle 116. The posterior recesses of upper and lower joint spaces 117, 118 have increased in size.

FIG. 3 is a schematic cross sectional view of a TMJ joint replacement apparatus in accordance with an embodiment of the invention. Specifically, FIG. 3 shows a cross-sectional view of a condyle assembly 340 and an articular eminence assembly 342 as implanted in the condyle 321 and articular eminence 320 respectively. In this embodiment, the condyle assembly 340 includes a base plate 323, an insert 324, and a surface plate 325.

The base plate 323 can be fitted within a groove formed in the condyle 321. The base plate can be formed of a biocompatible material. For example, the base plate can be formed of a biocompatible metal, polymer, ceramic, composite, glass, or the like. In various embodiments the base plate is a biocompatible metal. Exemplary biocompatible metals include, but are not limited to, titanium, cobalt, chromium, nickel, and alloys including one or more of the same such as nitinol, stainless steel. Exemplary biocompatible polymers can include, but are not limited to, polyethylenes, polyamides, polysulfones, polyphenysulfones, polyketones (such as polyether ether ketone), polyphenylenes, polystyrenes, polyvinyls, and the like. Exemplary biocompatible ceramics can include hydroxyapatite, zirconia ceramics, alumina ceramics, calcium phosphates, and the like. While not intending to be bound by theory, it is believed that the base plate 323 can osseointegrate with the bone of the condyle 321 over time after implantation. Osseointegration includes the direct structural and functional connection between living bone and the surface of the implant. In some embodiments the base plate 323 can include titanium and/or hydroxyapatite in order to facilitate osseointegration.

The insert 324 be disposed between the base plate 323 and the surface plate 325. The insert 324 can be configured to facilitate fastening of the surface plate 325 to the base plate 323. The insert 324 can be secured to the base plate 323 through the use of a friction fit mechanism, an adhesive, a fastener, or the like. The surface plate 325 can, in turn, be secured to the insert 324 through the use of a friction fit mechanism, an adhesive, a fastener, or the like. For example, in some embodiments, a fastener such as a locking tab structure can be used to removably secure the surface plate 325 to the insert 324. Other fasteners can include, but are not limited to, screws, rivets, bolts, crimping mechanisms, pins, sutures, wires, and the like.

The insert can be formed of various biocompatible materials including, but not limited to, biocompatible metals, polymers, ceramics, composites, glasses, and the like. In various embodiments, the insert is a biocompatible polymer. Exemplary biocompatible polymers can include, but are not limited to, polyethylenes, polyamides, polysulfones, polyphenysulfones, polyketones (such as polyether ether ketone), polyphenylenes, polystyrenes, polyvinyls, and the like.

The surface plate 325 can secured to the base plate 323, either directly or through the insert 324. The surface plate 325 can include a substantially convex surface 350. The surface plate 325 can be formed of a biocompatible material. For example, the surface plate 325 can be formed of a biocompatible metal, polymer, ceramic, composite, glass, or the like. In various embodiments the base plate is a biocompatible metal. Exemplary biocompatible metals include, but are not limited to, titanium, cobalt, chromium, nickel, and alloys including one or more of the same such as nitinol, stainless steel. Exemplary biocompatible polymers can include, but are not limited to, polyethylenes, polyamides, polysulfones, polyphenysulfones, polyketones (such as polyether ether ketone), polyphenylenes, polystyrenes, polyvinyls, and the like. Exemplary biocompatible ceramics can include hydroxyapatite, zirconia ceramics, alumina ceramics, calcium phosphates, and the like. In some embodiments, the surface plate 325 can include multiple materials. In some embodiments, the surface plate 325 can include a coating 355. By way of example, the coating 355 can be a ceramic. In some embodiments, the surface plate 325 can include a wear pad, such as a ceramic wear pad.

The articular eminence assembly includes a base plate 326, an insert 327, and a surface plate 328. The base plate 326 of the articular eminence assembly can be configured to fit within a groove formed in the articular eminence. The base plate 326 can be formed of various biocompatible materials such as biocompatible metals, polymers, ceramics, composites, glasses, or the like described above. While not intending to be bound by theory, it is believed that the base plate 326 can osseointegrate with the bone of the articular eminence 320 over time after implantation. In some embodiments the base plate 326 can include titanium and/or hydroxyapatite in order to facilitate osseointegration.

The insert 327 can be configured to facilitate fastening of the surface plate 328 to the base plate 326. The insert 327 can be formed of various biocompatible materials such as biocompatible metals, polymers, ceramics, composites, glasses, or the like described above. The surface plate 328 can include a surface with a substantially convex portion 341 and a substantially concave portion 343. The surface plate 328 can be formed of various biocompatible materials such as biocompatible metals, polymers, ceramics, composites, glasses, or the like described above. In some embodiments, the surface plate 328 can include multiple materials. In some embodiments, the surface plate 328 can include a coating 353. By way of example, the coating 353 can be a ceramic. In some embodiments, the surface plate 325 can include a wear pad, such as a ceramic wear pad.

After implantation, the surface plate 325 of the condyle assembly 340 can slide against the surface plate 328 of the articular eminence assembly 342. In various embodiments, sliding of the surface plate 325 of the condyle assembly 340 against the surface plate 328 of the articular eminence assembly 342 can allow for rotation and translation of the condyle allowing for movement of the jaw that mimics movement in a normal temporomandibular joint.

In various embodiments, attachment of the surface plate 325 or 328 to the insert 324 or 327 and/or to the base plate 323 or 326 can be reversible so that the surface plate 325 or 328 can be removable after implantation in the patient. As such, in some embodiments herein, the surface of the implant that is subject to wear can be replaced if needed without revising the entire implant.

Figure 4A:
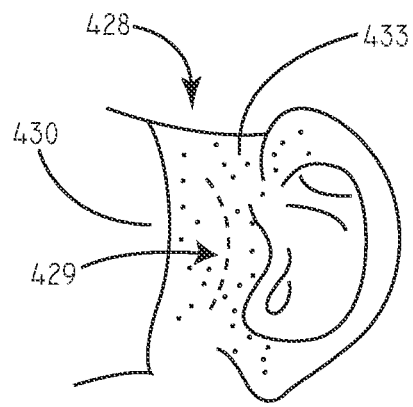
FIG. 4A is a schematic side view of the incision area that provides access to the posterior lateral aspect of the TMJ in accordance with various embodiments herein.

FIG. 4A is a schematic view of the left TMJ surgical incision area. In an embodiment of the invention, an incision 429 can be made in the preauricular region. In various embodiments, the incision can be made immediately anterior to the tragal cartilage. It will be appreciated that the incision may be of various sizes depending on the size of the patient, the skill and experience of the physician, the specific size of the condyle assembly and articular eminence assembly and the like. However, in various embodiments, the incision is less than or equal to about 25 mm in length. Surgical drapes 430 can be used in order to limit exposure of the skin 433.

Figure 4B:
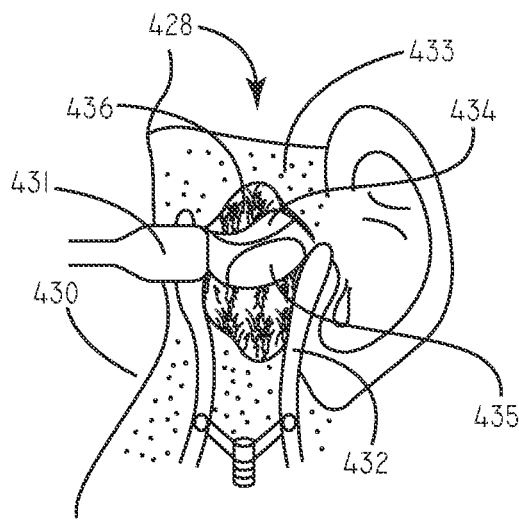
FIG. 4B is a schematic side view of the microscopic surgical exposure of the posterior lateral aspect of the TMJ after formation of an incision in accordance with various embodiments herein.

FIG. 4B is a schematic view of the microscopic surgical exposure 428 in the left preauricular region after the incision has been made and retractors 431, 432 have been applied. The articular eminence 434 and condyle 435 below are exposed as well as adjacent soft tissues 436. In this view, the wound has been distracted with retractors 431 and 432. In various embodiments, the TMJ disk can be removed as part of the procedure for total joint replacement. In FIG. 4B the disk is shown removed. It will be appreciated that in various embodiments the surgery can be conducted as microscopic minimally invasive procedure. In many embodiments, the use of an operating microscope can be used in order to aid the physician in conducting the procedure.

Figure 5:
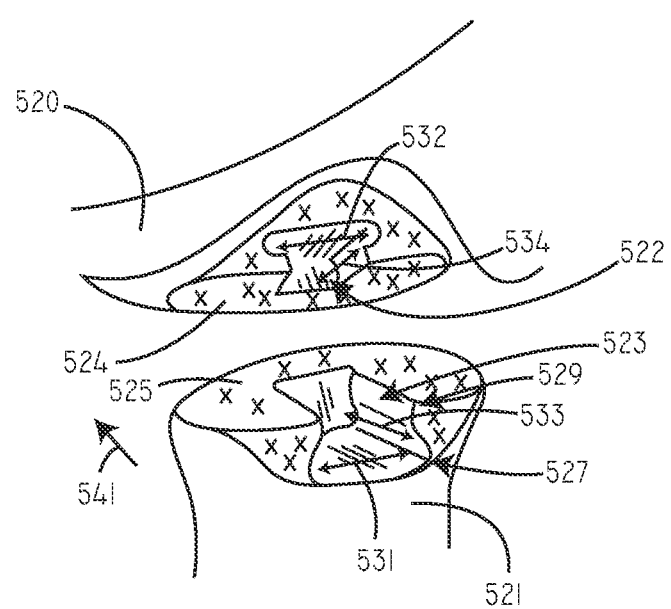
FIG. 5 is a schematic perspective posterior lateral view of preparation of condyle and articular eminence bone stock in order to receive implant structures in accordance with various embodiments herein.

In various embodiments, bone can be removed from the condyle head to form a bone surface defining a groove. FIG. 5 is a schematic perspective view of the articular eminence 520 and condyle 521 in which bone removal has been carried out. Surgical tools such as a microfile, or the like, can be used in order to form groove 523 in the head of the condyle. A relatively flat platform 525 or shelf can also be formed. In some embodiments, the groove 523 can pass all the way through the condyle 521 head in a posterior to anterior direction (in the direction of arrow 541). In other embodiments, the groove 523 may terminate before passing all the way through to the anterior side of the condyle 521 head. In still other embodiments, the groove 523 can be oriented lateral to medial. In various embodiments, the groove 523 can be wider at its base 527 than at the top 529 of the groove 523. The groove 523 can have various specific dimensions. However, in some embodiments the width at its widest point 531 can be from about 4 millimeters to about 7 millimeters. The length 533 of the groove 523 can be from about 6 millimeters to about 10 millimeters, depending on whether or not the groove 523 passes all the way through the condyle 521 head.

Similarly, bone can be removed from the articular eminence 520 to form a bone surface 524 defining a groove 522. In some embodiments, the groove 522 can pass all the way through the articular eminence 520 in a posterior to anterior direction. In other embodiments, the groove 522 may terminate before passing all the way through to the anterior side of the articular eminence 520. In still other embodiments, the groove 522 can be oriented substantially perpendicularly to the posterior to anterior axis (e.g., can be oriented left to right or right to left). In various embodiments, the groove 522 can be wider at its base than at the top of the groove 522. The groove 522 can have various specific dimensions. However, in some embodiments the width at its widest point 532 can be from about 4 millimeters to about 7 millimeters. The length 534 of the groove 522 can be from about 6 millimeters to about 10 millimeters, depending on whether or not the groove 522 passes all the way through the articular eminence 520.

Figure 6:
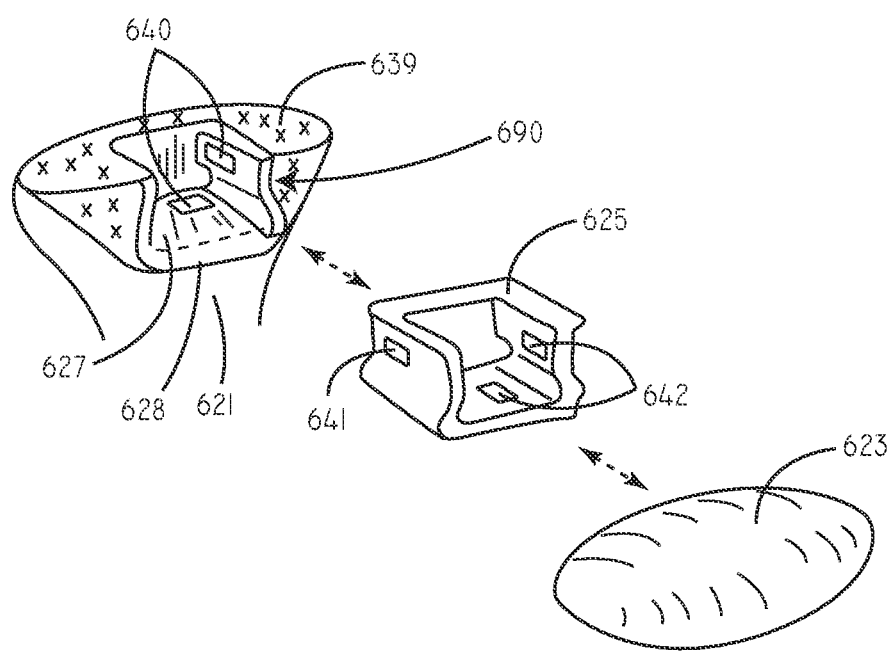
FIG. 6 is an exploded schematic perspective posterior lateral view of condyle assembly elements in accordance with various embodiments herein.

FIG. 6 shows an exploded perspective posterior lateral view of a condyle assembly and how it can be inserted into a groove 690 on the condyle head 621. The condyle head 621 can be prepared by removing bone to form the groove 690 and a flat bone surface 639. The base plate 627 can then be inserted into the groove 690. The groove 690 can be sized so that there is a tight fit between the base plate 627 and the groove 690. In some embodiments, the base plate 627 can include a flange 628 that is positioned so that the base plate 627 can only be inserted a certain distance into the groove before the flange physically prevents further insertion. The flange 628 can extend away from the base plate 627 in a direction opposite the surface plate. In some embodiments, the surfaces of the base plate 627 that will be in contact with the bone surface can be treated in order to facilitate osseointegration. For example, in some embodiments a porous material can be deposited on the base plate 627 that facilitates osseointegration. In some embodiments, an active agent can be deposited on the base plate 627 that facilitates osseointegration. In some embodiments, the base plate 627 can include indentations 640 on its inner surface that can be configured to receive locking tabs or other fasteners on the insert 625 and/or on the surface plate 623.

The insert 625 can fit within the base plate 627, which itself can be at least partially within the groove 690 in the condyle 621 head. The insert 625 can include one or more outside tabs 641 can fit within the indentations 640 on the base plate 627. The outside tabs 641 can serve to secure the insert 625 to the base plate 627. The insert 625 can also include one or more inside tabs 642. The inside tabs 642 can serve to secure the insert 625 to the surface plate 623. The surface plate 623 can include one or more indentations 642 that correspond to the inside tabs 642 on the insert 625. In some embodiments, the base plate 627 can be inserted into the groove 690, then the insert 625 can be inserted into the base plate 627, and then the surface plate 623 can be inserted into the insert 625. However, in other embodiments the elements of the condyle assembly can be assembled in a different order. For example, in some embodiments, the base plate 627 and the insert 625 can be attached together and then both elements can be inserted into the groove 690. In other embodiments, the base plate 627 can be inserted into the groove 690, then the insert 625 can be attached to the surface plate 623, then the combined insert 625 and surface plate 623 can be inserted into the groove 690. Other orders of assembly are also contemplated.

Figure 7:
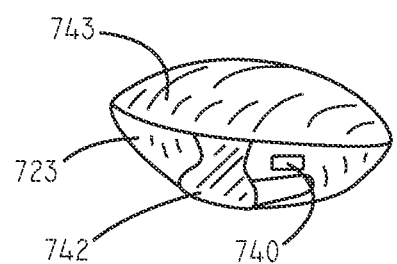
FIG. 7 is a schematic perspective view of the surface plate as viewed from an anterior lateral perspective.

FIG. 7 is a schematic perspective view of a surface plate 723 as viewed from an anterior lateral perspective. In this view, the convex surface 743 of the surface plate 723 is visible along with the tongue 742 that is configured to fit within the corresponding recess of the insert and/or the base plate. One or more indentations 740 can be disposed on the surface of the tongue 742 in order to accommodate locking tabs from the insert.

Figure 8:
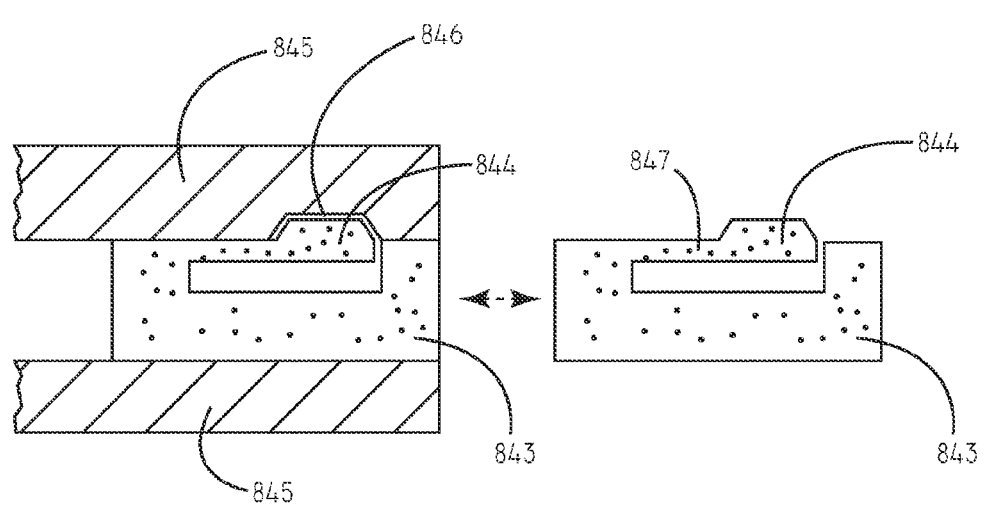
FIG. 8 is a schematic view of an exemplary locking mechanism.

It will be appreciated that there are many different specific configurations that are possible for use as a locking tab. As merely one example, FIG. 8 is a cross-sectional view of an exemplary locking tab structure. In this view a first structure 843 that defines a locking tab 844 is shown as it is inserted into a second structure 845 that defines an indentation 846 to receive the locking tab 844. As the first structure 843 is physically inserted into the second structure 845, the arm 847 of the locking tab 844 deflects and then releases after the locking tab 844 is positioned within the second structure 845 and beneath the indentation 846. A first amount of force is necessary to insert the first structure 843 within the second structure 845. After the locking tab 844 is seated within the indentation 846, a certain amount of force is then required to remove the first structure 843 from the second structure 845.

Figure 9:
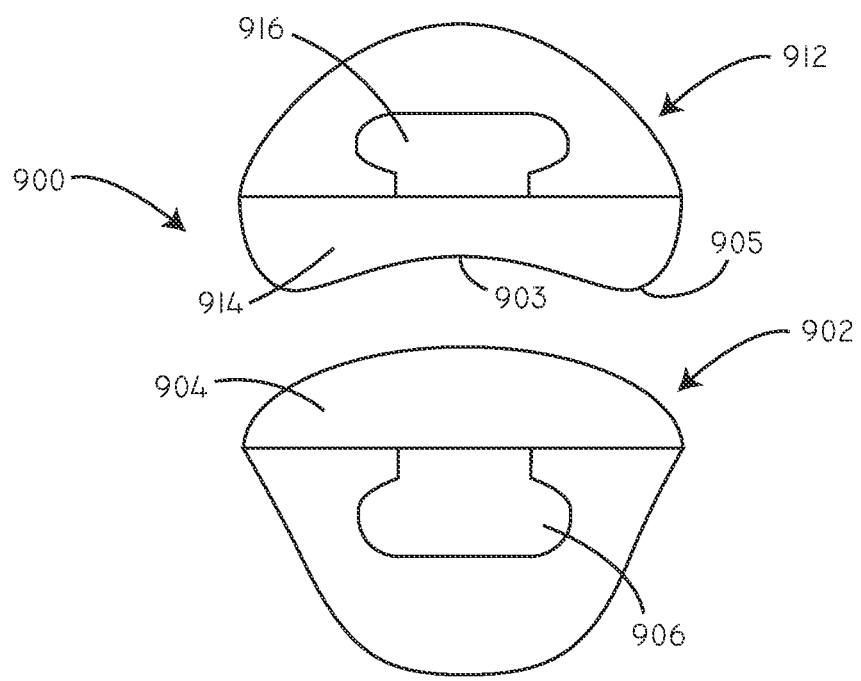
FIG. 9 is a schematic front view (anterior side) of an apparatus for treating dysfunction of the TMJ in accordance with another embodiment of the invention.

It will be appreciated that in various embodiments a more limited number of parts may be used to form an apparatus for treating dysfunction of the TMJ. By way of example, in some embodiments, the base plate, insert, and surface plate can be effectively integrated into a single part for one or both of the condyle assembly and the articular eminence assembly. Referring now to FIG. 9, a schematic front view is shown of an apparatus 900 for treating dysfunction of the TMJ. In this embodiment, the condyle assembly 902 includes a single piece including a tongue 906 to fit within a corresponding groove in the condyle. The condyle assembly 902 further includes a convex top surface 904. The apparatus 900 further includes a articular eminence assembly 912 including a single piece including a tongue 916 to fit within a corresponding groove in the articular eminence. The articular eminence assembly 912 further includes a top surface 914 having at least a portion that is convex. In some embodiments, the top surface 914 of the articular eminence assembly 912 can also include a portion 903 that is depressed relative to the peripheral edges 905 forming a recess into which the top surface 904 of the condyle assembly can fit.

Figure 10:
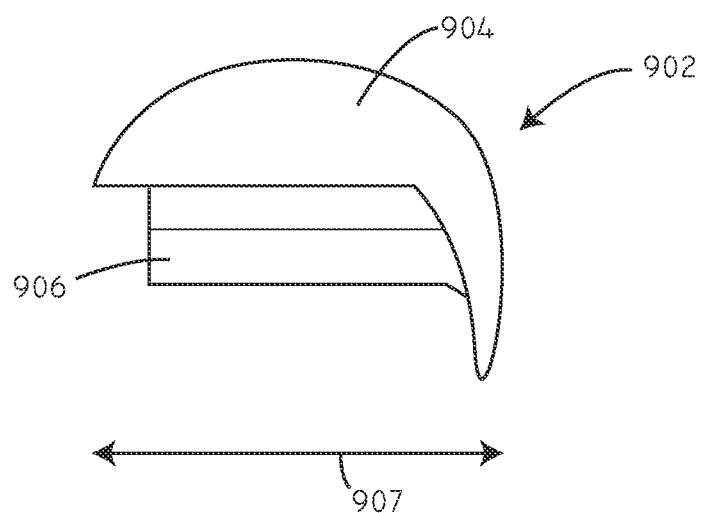
FIG. 10 is a schematic side view of the condyle assembly of FIG. 9.
Figure 11:
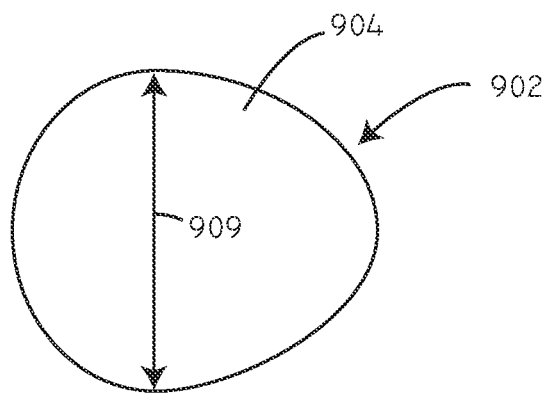
FIG. 11 is a schematic top view of the condyle assembly of FIG. 9.

FIG. 10 is a schematic side view of the condyle assembly 902 of FIG. 9. The condyle assembly 902 can have a length similar to other embodiments included herein. For example, the condyle assembly 902 can have a length 907 of about 8 millimeters to about 14 millimeters. FIG. 11 is a schematic top view of the condyle assembly of FIG. 9. The condyle assembly 902 can have a width similar to other embodiments included herein. For example, the condyle assembly 902 can have a width 909 of about 16 millimeters to about 22 millimeters.

Figure 12:
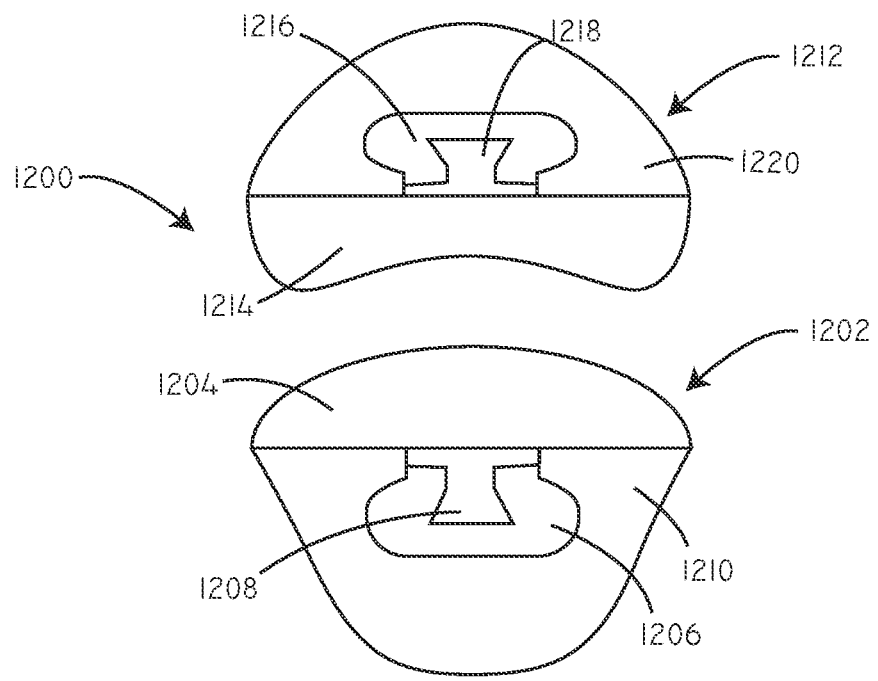
FIG. 12 is a schematic front view (anterior side) of an apparatus for treating dysfunction of the TMJ in accordance with another embodiment of the invention.

In still other embodiments, one or both of the condyle assembly and the articular eminence assembly can take the form of a two piece structure. Referring now to FIG. 12, a schematic front view is shown of an apparatus 1200 for treating dysfunction of the TMJ. In this embodiment, the condyle assembly 1202 includes a base plate 1206 and a surface plate 1210. The surface plate 1210 can be secured to the base plate 1206 with a locking tab 1208. However, it will be appreciated that various other structures for securing the surface plate 1210 to the base plate 1206 are also contemplated. The surface plate 1210 can include a substantially convex top surface 1204. Similarly, in this embodiment, the articular eminence assembly 1212 can include a two piece structure. Specifically, the articular eminence assembly 1212 can include a surface plate 1220 and a base plate 1216. The surface plate 1220 can be secured to the base plate 1216 with a locking tab 1218. The surface plate 1220 can include a substantially convex portion (facing inward toward the joint) surface 1214.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as "arranged", "arranged and configured", "constructed and arranged", "constructed", "manufactured and arranged", and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

This application is intended to cover adaptations or variations of the present subject matter. It is to be understood that the above description is intended to be illustrative, and not restrictive. The scope of the present subject matter should be determined with reference to the appended claims, along with the full scope of equivalents to which such claims are entitled.

What is claimed is:

1. An apparatus for treating dysfunction of the temporomandibular joint comprising:
    a base plate, the base plate configured to fit within a groove formed in a condyle of a patient;
    a surface plate comprising a substantially convex surface;
    an insert configured to fit between the base plate and the surface plate, configured to facilitate locking of the surface plate to the base plate; the insert comprising a polymeric material, and
    a second base plate, the second base plate configured to fit within a groove formed in an articular eminence of the patient;
    a second surface plate comprising a surface having a convex portion; and
    a second insert configured to fit between the second base plate and the second surface plate, configured to facilitate locking of the second surface plate to the second base plate, the second insert comprising a polymeric material;
    wherein the surface plate and the second surface plate are configured to slidably engage one another to allow for rotation and translation of the condyle of the patient.

2. The apparatus of claim 1, the base plate and the surface plate comprising a biocompatible metal.

3. The apparatus of claim 1, the insert comprising a fastener.

4. The apparatus of claim 3, the fastener comprising a tab.

5. The apparatus of claim 1, the surface plate having a first outer surface, the second surface plate having a second outer surface; the first outer surface and the second outer surface having different shapes in cross-section.

6. The apparatus of claim 5, the second outer surface having an S-curve shape in cross-section.

* * * * *